(12) United States Patent
Tseng (10) Patent No.: US 8,853,571 B2
(45) Date of Patent: Oct. 7, 2014

(54) FOOT SWITCH HAVING SECURITY MECHANISM

(75) Inventor: Kuan-Shu Tseng, New Taipei (TW)

(73) Assignee: Timotion Technology Co., Ltd., New Taipei (TW)

( * ) Notice: Subject to any disclaimer, the term of this patent is extended or adjusted under 35 U.S.C. 154(b) by 230 days.

(21) Appl. No.: 13/429,379

(22) Filed: Mar. 25, 2012

(65) Prior Publication Data

US 2013/0168212 A1   Jul. 4, 2013

(30) Foreign Application Priority Data

Jan. 10, 2012   (TW) .............................. 101101010 A (51) Int. Cl.
*H01H 3/14*   (2006.01)
(52) U.S. Cl.
USPC ....................................................... 200/86.5
(58) Field of Classification Search
CPC ....... H01H 13/00; H01H 13/04; H01H 13/16; H01H 2013/00; H01H 2013/04; H01H 2013/06; H01H 2013/566; H01H 2223/02; H01H 2233/05; H01H 2233/07
USPC ........... 200/43.13, 302.2, 5 A, 293, 86.5, 5 C, 200/5 D, 50.32, 50.36
See application file for complete search history.

(56) References Cited

U.S. PATENT DOCUMENTS

| | | | | |
|---|---|---|---|---|
| 3,963,890 A | * | 6/1976 | Straihammer | 200/86.5 |
| 5,422,521 A | * | 6/1995 | Neer et al. | 307/119 |
| 6,866,507 B2 | * | 3/2005 | Beerstecher | 433/101 |
| 7,990,366 B2 | | 8/2011 | Logue | |

FOREIGN PATENT DOCUMENTS

EP   1707147 B1   6/2011

OTHER PUBLICATIONS

Taiwan Office Action issued on Mar. 6, 2014.

* cited by examiner

*Primary Examiner* — Renee Luebke
*Assistant Examiner* — Anthony R. Jimenez
(74) *Attorney, Agent, or Firm* — Chun-Ming Shih; HDLS IPR Services (57) ABSTRACT

A foot switch having a security mechanism includes a main body, a circuit board, a pedal and a latch. The circuit board is received in the main body. The pedal is provided on the main body. The latch is provided adjacent to the pedal. The pedal is electrically connected to the circuit board via the latch. When the latch and the pedal are pressed, the circuit board is electrically connected to the pedal. The pedal can only generate an unlocking action via the latch, whereby the circuit board is electrically connected to the pedal to output a driving signal. Thus, the foot switch of the present invention can be prevented from being stepped on by mistake, thereby enhancing the safety in use.

12 Claims, 10 Drawing Sheets

FOOT SWITCH HAVING SECURITY MECHANISM

BACKGROUND OF THE INVENTION

1. Field of the Invention

The present invention relates to a switch control structure, and in particular to a foot switch having a security mechanism.

2. Description of Prior Art

In a medical instrument such as a sickbed or a clinic chair, its height or inclination angle often needs to be adjusted to fit the build or demands of a user, so that a patient lying or sitting thereon can feel more comfortable. Since a doctor often performs a medical treatment by his/her both hands, a foot-operated switch (referred to as a "foot switch" hereinafter) is usually provided, whereby the doctor can perform the medical treatment while adjust the height and inclination angle of the sickbed or clinic chair in a convenient and controlled manner.

The conventional foot switch includes a switch box and a pedal. The interior of the switch box is provided with a switch. The pedal has a recovering plate which can recover to its original state automatically. When the pedal is stepped on, the recovering plate presses the switch in the switch box via a pushing rod, thereby transmitting a driving signal. By stepping on the foot switch, the driving signal can be transmitted to the sickbed or the clinic chair to thereby control the height and inclination angle of the sickbed or the clinic chair.

However, in practice, the above conventional foot switch has a big risk that it lacks a security mechanism. More specifically, when a doctor, a nurse or an operator is busy or absentminded and neglects the current position of the foot switch, he/she may step on the foot switch carelessly while his/her hands are still working, which may cause an accident. Even, the life of the patient or the operator may be thus threatened.

In view of the above, the present Inventor aims to solve the above problems based on his expert knowledge and deliberate researches.

SUMMARY OF THE INVENTION

The present invention is to provide a foot switch having a security mechanism, in which a latch can only generate an unlocking action via a latch to thereby electrically connect a circuit board and the pedal to output a driving signal. In this way, the foot switch can be prevented from being stepped on by mistake. Thus, the foot switch of the present invention has an improved safety in use.

The present invention provides a foot switch having a security mechanism, which includes a main body, a circuit board disposed in the main body, a pedal disposed on the main body, and a latch provided adjacent to the pedal. The pedal is electrically connected to the circuit board via the latch. When the latch and the pedal are pressed, the pedal is electrically connected to the circuit board.

The present invention provides a foot switch having a security mechanism, which includes a main body, a circuit board disposed in the main body, a pedal disposed on the main body, a latch provided adjacent to the pedal, and a processor. The pedal and the latch are electrically connected to the circuit board via the processor. The pedal is pressed to output a first trigger signal. The latch is pressed to output a second trigger signal. When the processor receives the first trigger signal and the second trigger signal, the pedal is electrically connected to the circuit board.

The present invention has advantageous features as follows. The pedal can only generate an unlocking action via the latch. That is, only when the latch and the pedal are pressed simultaneously, the electrical connection between the pedal and the circuit board can be achieved to output a driving signal, thereby controlling the height or inclination angle of a sickbed or clinic chair. By this structure, the foot switch can be prevented from being stepped on by mistake when the operator is busy or absentminded. Thus, the foot switch of the present invention has an improved safety in use.

Further, a pressing button is location at a higher position. A first key and a second key are located at a lower position respectively. Such an arrangement conforms to ergonomics, so that the sole of the foot of the operator can step on the foot switch of the present invention easily. Further, since the pressing button is located at a position higher than the first key and the second key, the operator will not press the pressing button and the first key (or the second key) at the same time by mistake, so that the possibility of erroneously stepping on the foot switch can be reduced. Thus, the foot switch of the present invention has an improved safety in use.

Since the first key and the second key support most of the weight of the foot, the annular block, the first block and the second block are formed into an annular shape respectively and engaged with each other, thereby increasing the supporting capacity of the first key and the second key and the combining stability among the first key, the second key and the main body. Thus, the foot switch of the present invention generates a good efficiency in use.

Further, in an another embodiment of the foot switch of the present invention, the pedal and the latch generate an unlocking action via the latch. By pressing the latch and the pedal respectively, the processor receives a first trigger signal and a second trigger signal respectively, the circuit board and the pedal are electrically connected to each other to output a driving signal for controlling the height and inclination angle of the sickbed or clinic chair. Thus, the problem that the foot switch may be stepped on by mistake when the operator is busy or absentminded can be prevented. Thus, the foot switch of the present invention has an improved safety in use.

DETAILED DESCRIPTION OF THE INVENTION

The detailed description and technical contents of the present invention will become apparent with the following detailed description accompanied with related drawings. It is noteworthy to point out that the drawings is provided for the illustration purpose only, but not intended for limiting the scope of the present invention.

Figure 1:
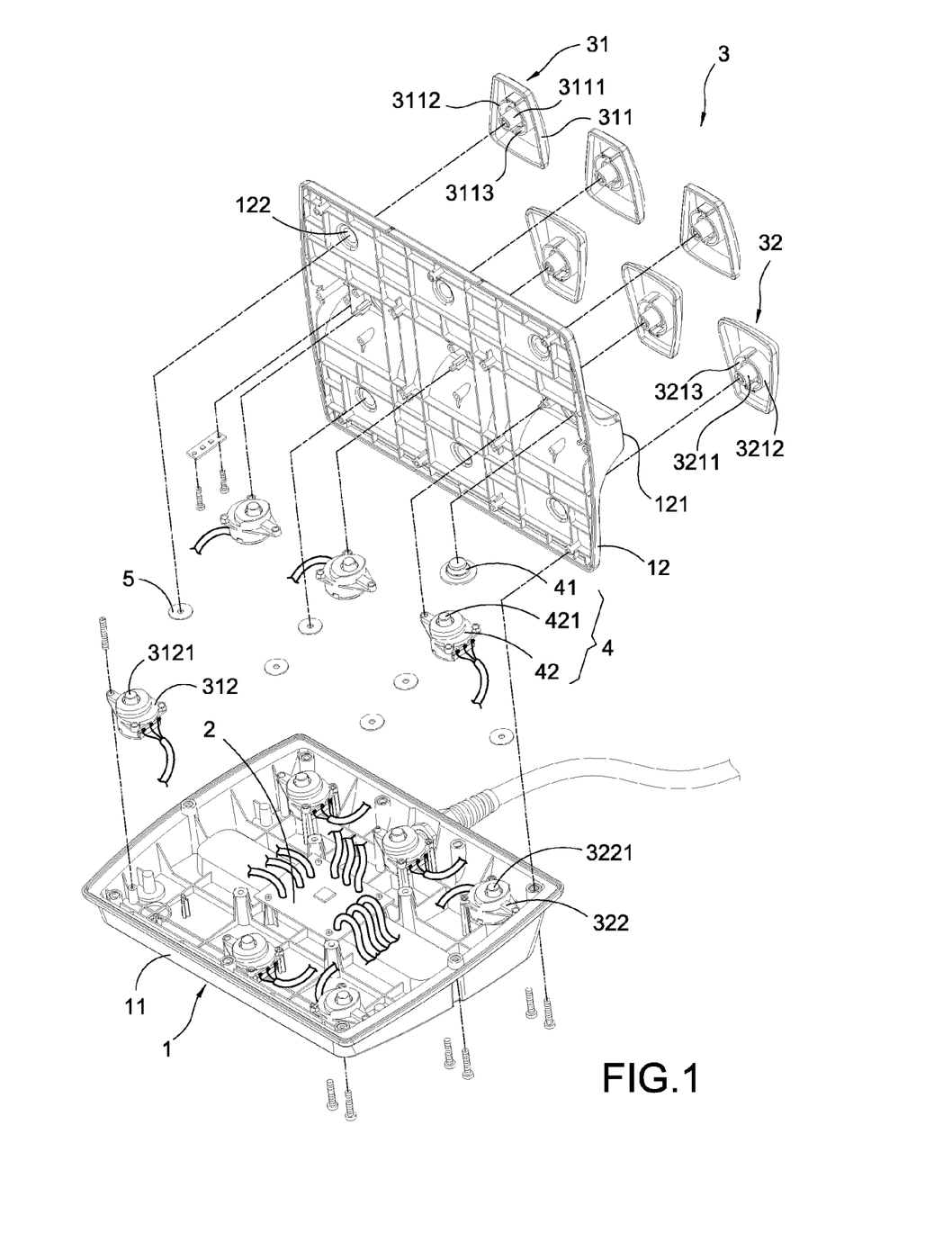
FIG. 1 is an exploded perspective view showing the foot switch according to the present invention.
Figure 2:
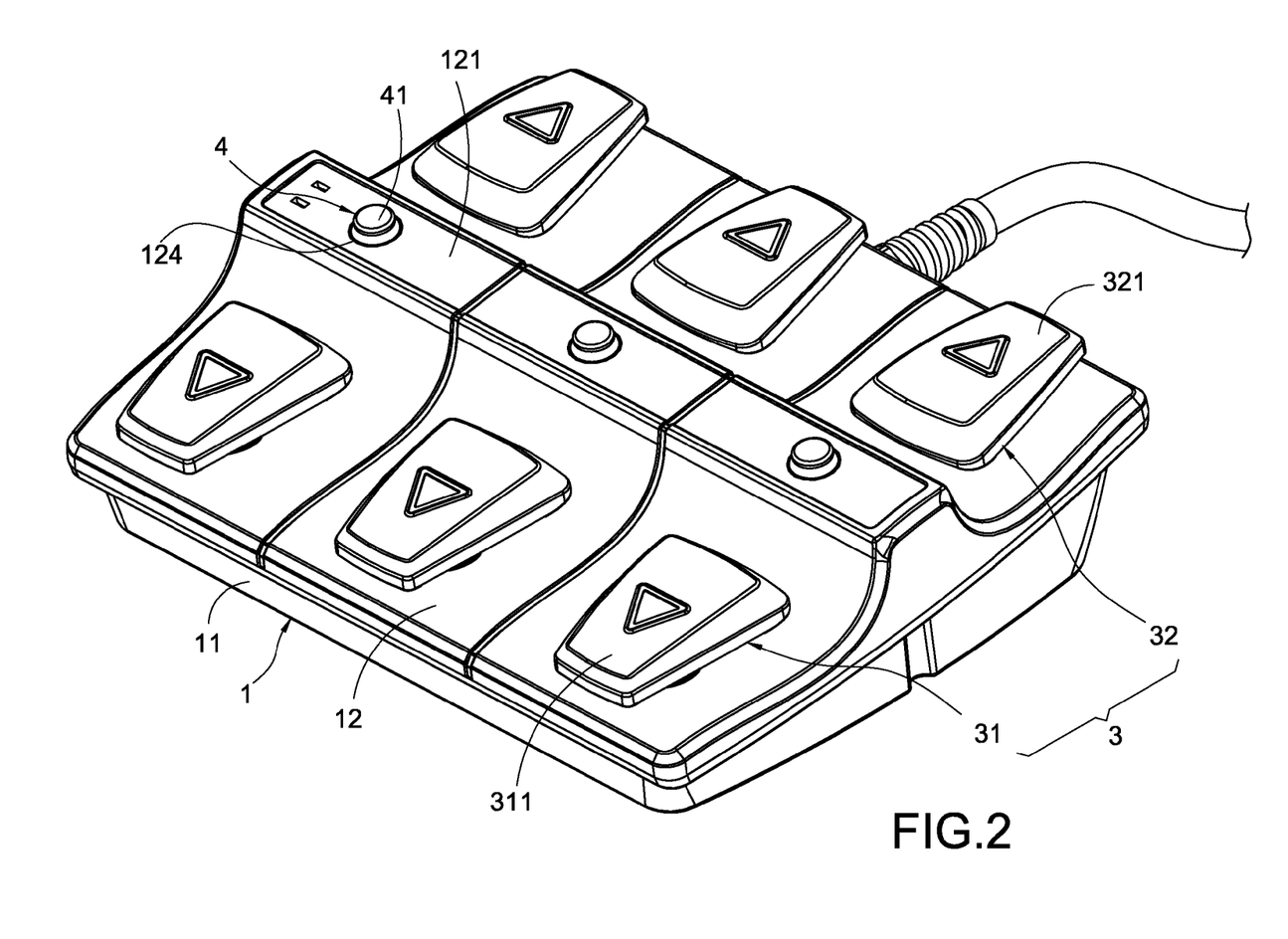
FIG. 2 is an assembled perspective view showing the foot switch according to the present invention.
Figure 3:
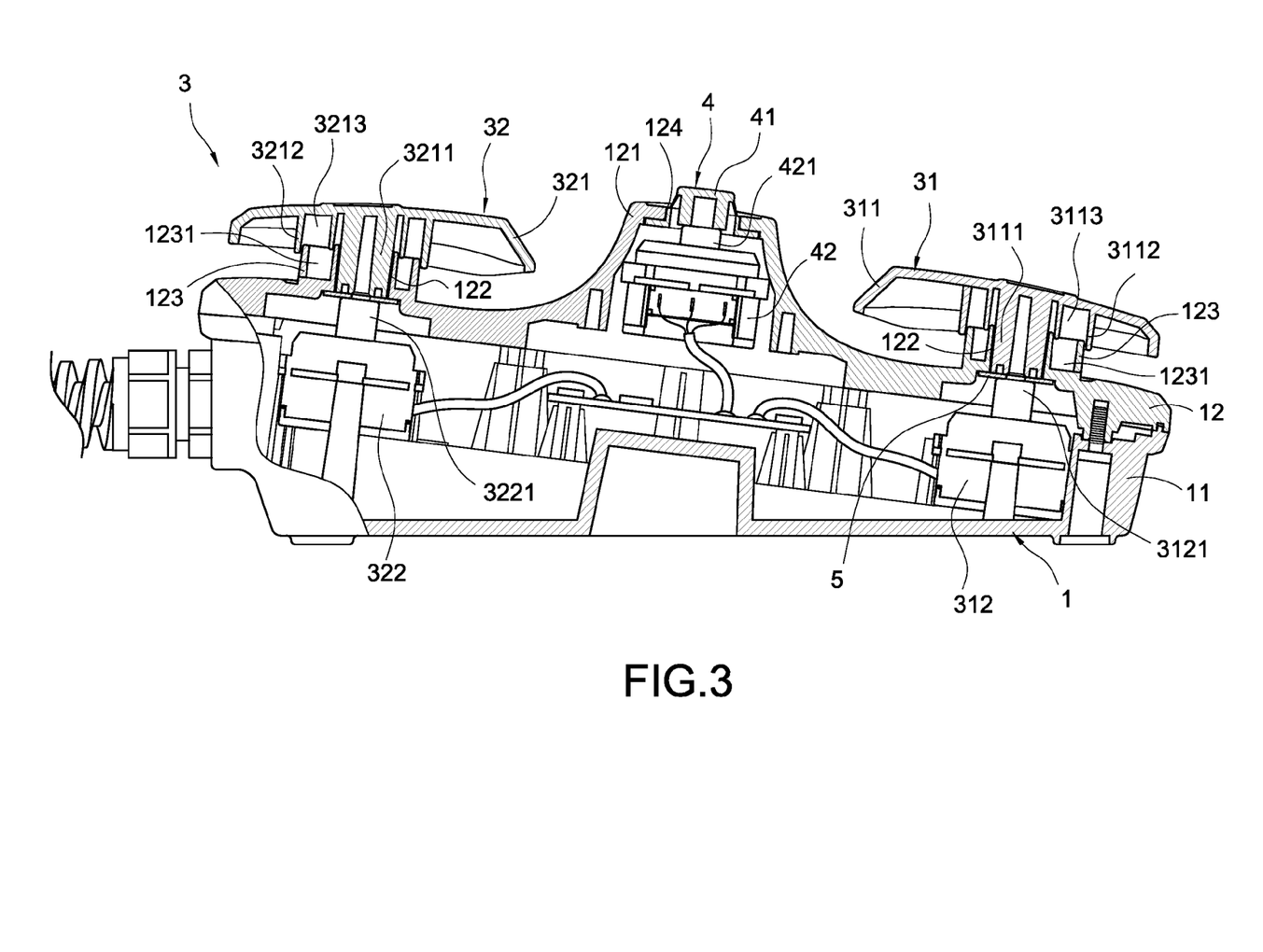
FIG. 3 is a cross-sectional view showing the foot switch according to the present invention.

Please refer to FIGS. 1 to 3. The present invention relates to a foot switch having a security mechanism. The foot switch includes a main body 1, a circuit board 2, a pedal 3 and a latch 4.

The main body 1 comprises a base 11 and a cover 12 covering the base 11. The center of the cover 12 has a protruding section 121. The cover 12 is provided with a plurality of through-holes 122 on both sides of the protruding section 121. The outer edge of each through-hole 122 is provided with an annular block 123. The cover 12 is provided at the protruding section 121 with one or a plurality of penetration holes 124. The circuit board 2 is received in the main body 1.

The pedal 3 is provided on the main body 1. The pedal 3 comprises at least one first adjusting assemblies 31 and at least one second adjusting assemblies 32. Each first adjusting assembly 31 comprises a first key 311 and a first trigger switch 312 connected to each other. Each first trigger switch 312 has a first recovering portion 3121. Each second adjusting assembly 32 comprises a second key 321 and a second trigger switch 322 connected to each other. Each second trigger switch 322 has a second recovering portion 3221.

The first key 311 and the second key 321 are exposed to main body 1. That is, each first key 311 and each second key 321 are exposed to both sides of the cover 12 relative to the protruding section 121. Each first trigger switch 312 and each second trigger switch 322 are accommodated in the base 11 and electrically connected the circuit board 2. More specifically, each first key 311 has a first supporting post 3111 and a first protruding block 3112 extending from the outer edge of the first supporting post 3111. Each first protruding block 3112 is provided a first trough 3113. Each first supporting post 3111 is disposed through each through-hole 122. The first key 311 passes through the through-hole 122 and abuts against the first recovering portion 3121. The annular block 123 and the first protruding block 3112 are engaged with the first trough 3113 via the annular groove 1231. Each second key 321 has a second supporting post 3211 and a second protruding block 3212 extending from the outer edge of the second supporting post 3211. Each second protruding block 3212 is provided with a second trough 3213. Each second supporting post 3211 is disposed through the penetration hole 122. The second key 321 passes through the through-hole 122 and abuts against the second recovering portion 3221. The annular block 123 and the second protruding block 3212 are engaged with the second trough 3213 via the annular groove 1231.

The number of the latch 4 is one or plural. The pedal 3 is electrically connected to the circuit board 2 via the latch 4. Each latch 4 is disposed adjacent to the pedal 3. More specifically, each latch 4 is provided on the main body 1 and is disposed between the first key 311 and the second key 321. The pressing button 41 is exposed to the protruding section 121. Each latch 4 comprises a pressing button 41 and a pressing switch 42 connected to each other. The pressing button 41 is provided on the protruding section 121. The pressing switch 42 is received in the base 11 and electrically connected to the circuit board 2. The pressing switch 42 has a recovering portion 421. The pressing button 41 abuts against the recovering portion 421 via the penetration hole 124. When the latch 4 and the first key 311 are pressed, the circuit board 2 is electrically connected to the pedal 3.

The present invention further includes two or a plurality of gaskets 5. a portion of the gaskets 5 are sandwich between the first key 311 and the first recovering portion 3121. The other portion of the gaskets 5 are sandwiched between the second key 321 and the second recovering portion 3221.

In the foot switch having a security mechanism according to the present invention, the circuit board 2 is disposed in the main body 1. The pedal 3 is disposed on the main body 1. Further, the latch 4 is disposed adjacent to the pedal 3. The pedal 3 is electrically connected to the circuit board 2 via the latch 4. When the latch 4 and the pedal 3 are pressed, the pedal 3 is electrically connected to the circuit board 2. The pedal 3 can only generate an unlocking action via the latch 4. That is, only when the latch 4 and the pedal 3 are pressed simultaneously, the pedal 3 and the circuit board 2 can be electrically connected to each other to output a driving signal to thereby control the height and inclination angle of a sickbed or a clinic chair. Thus, the problem that the foot switch may be stepped on by mistake when the operator is busy or absentminded can be prevented. Thus, the foot switch of the present invention has an improved safety in use.

Figure 4:
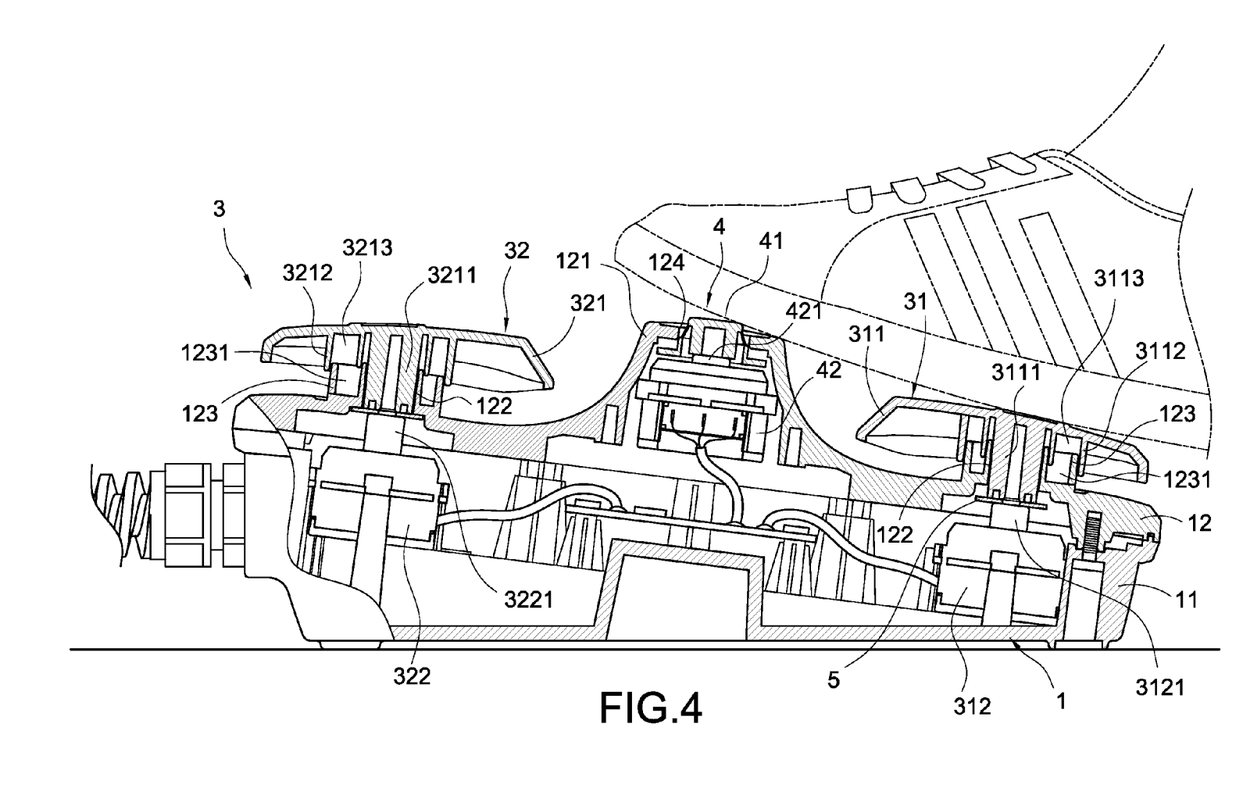
FIG. 4 is a schematic view showing the operating state of the foot switch according to the present invention.
Figure 5:
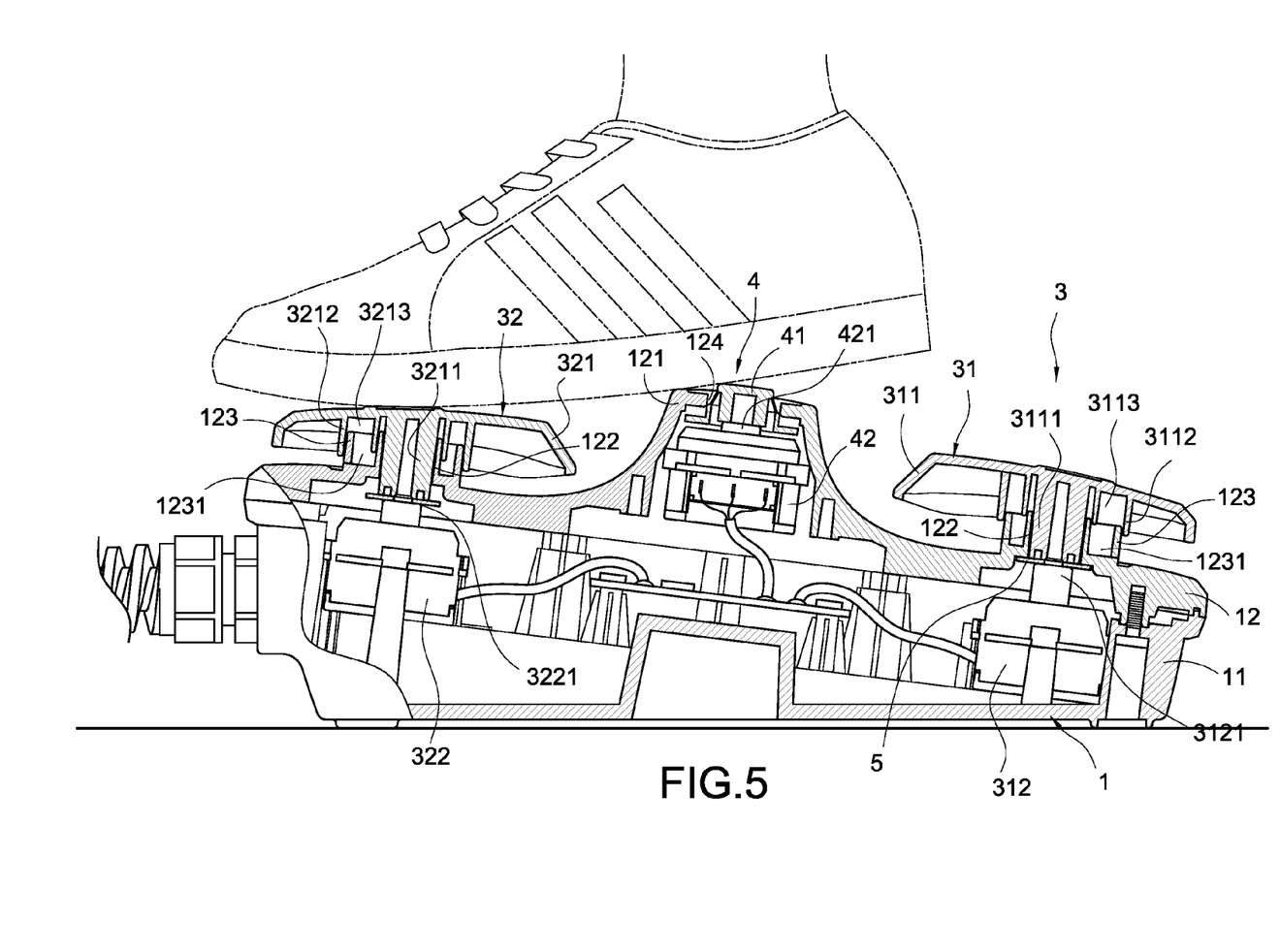
FIG. 5 is another schematic view showing the operating state of the foot switch according to the present invention.
Figure 6:
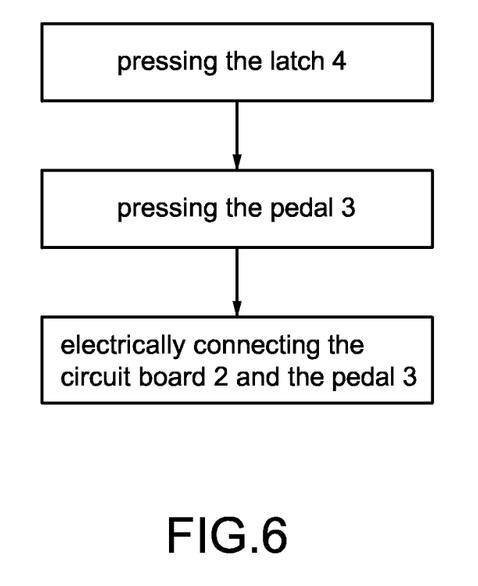
FIG. 6 is a block view showing the operation of the foot switch of the present invention.

Please refer to FIGS. 4 to 6, which show the operating state of the foot switch of the present invention. The reason why the pedal 3 can only generate an unlocking action via the latch 4 will be described as follows. An operator steps on the pressing button 41 of the latch 4, so that the recovering portion 421 moves downwardly to be electrically connected to the circuit board 2. At the same time, the operator also steps on the first key 311 or the second key 321 of the pedal 3, so that the first recovering portion 3121 or the second recovering portion 3221 moves downwardly to be electrically connected to the circuit board 2. As a result, the circuit board 2 is electrically connected to the pedal 3. At this time, stepping on the first key 311 or the second key 321 outputs a driving signal to thereby control the height or inclination angle of a sickbed or a clinic chair.

The pressing button 41 is provided on the protruding section 121 in the center of the cover 12 in such a manner that the pressing button 41 is located at a higher position whereas the first key 311 and the second key 321 are located at a lower position. Such a structure conforms to ergonomics, so that the sole of the foot of the operator can step on the foot switch easily. At the same time, the position of the pressing button 41 is higher than the position of the first key 311 and the second key 321. Thus, the operator will not simultaneously press the pressing button 41 and the first key 311 (or the second key 321) by mistake easily, so that the possibility of stepping on the foot switch by mistake can be reduced. Therefore, the present invention has an improved safety in use.

The first key 311 has a first supporting post 3111 and a first protruding block 3112 extending from the periphery of the first supporting post 3111. The first protruding block 3112 is provided with a first trough 3113. The annular block 123 and the first protruding block 3112 are engaged with the first trough 3113 via the annular trough 1231. By this arrangement, since the first key 311 is disposed at the lower position, the first key 311 supports most of the weight of the foot. Further, since the annular block 123 and the first protruding block 3112 are formed into an annular shape respectively band engaged with each other, the supporting capacity of the first key 311 and the combining stability of the first key with the main body 1 can be enhanced. Thus, the foot switch having a security mechanism according to the present invention can achieve a good efficiency in use. The second key 321 has the second supporting post 3211 and the second protruding block 3212 extending from the periphery of the second supporting post 3211. The second protruding block 3212 is provided with a second trough 3213. The annular block 123 and the second protruding block 3212 are engaged with the second trough 3213 via the annular groove 1231. This structure can achieve the same effect as the above.

Figure 7:
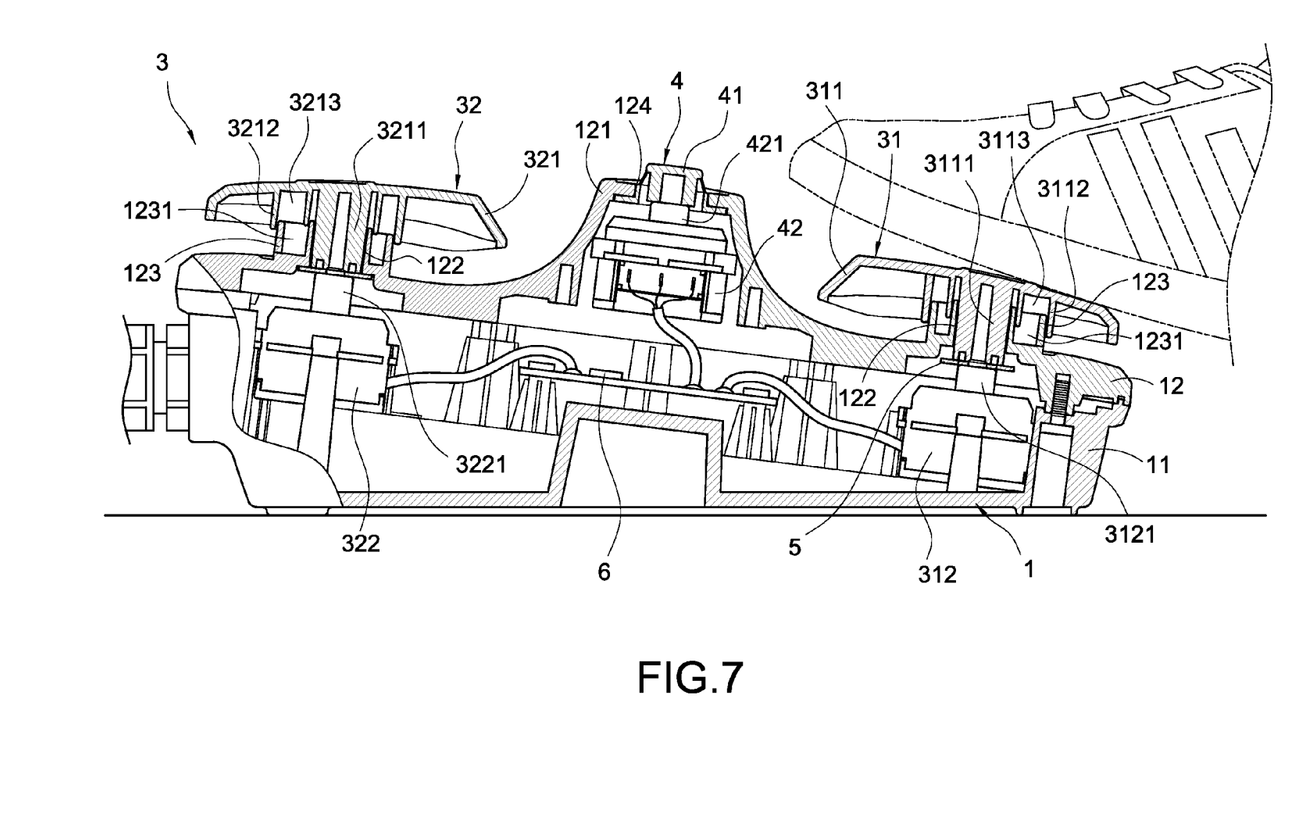
FIG. 7 is a schematic view showing the operating state of the foot switch according to another embodiment of the present invention.
Figure 8:
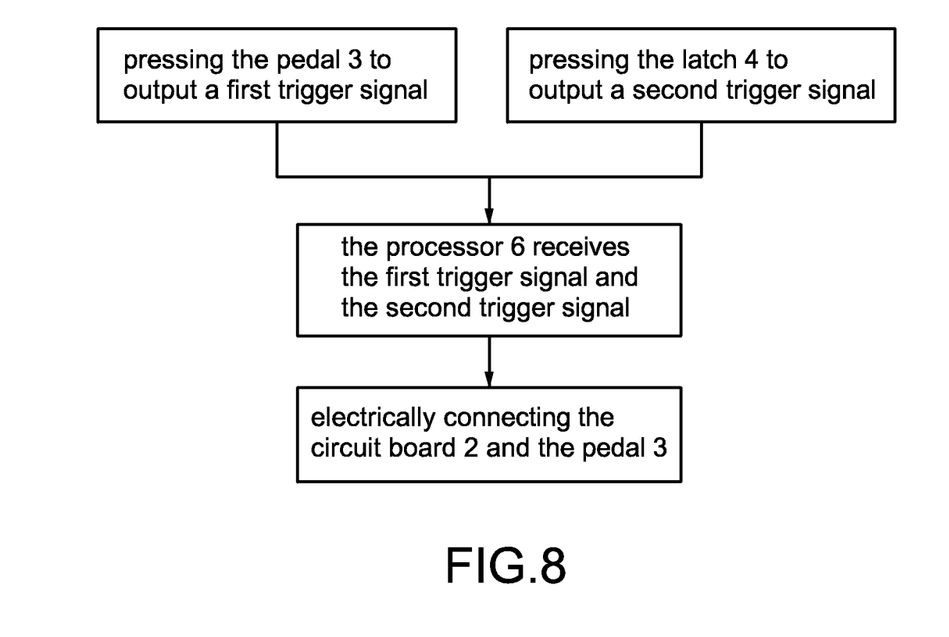
FIG. 8 is a block view showing the operation of the foot switch according to another embodiment of the present invention.

Please refer to FIGS. 7 to 8, which show another embodiment of the present invention. The foot switch of the present embodiment includes a main body 1, a circuit board 2, a pedal 3, a latch 4, and a processor 6.

The circuit board 2 is provided in the main body 1. The pedal 3 is provided on the main body 1. The latch 4 is provided adjacent to the pedal 3. The pedal 3 and the latch 4 are electrically connected to the circuit board 2 via the processor 6. When the pedal 3 is pressed, a first trigger signal is outputted. When the latch 4 is pressed, a second triggering signal is outputted. When the processor 6 receives the first trigger signal and the second trigger signal, the circuit board 2 is electrically connected to the pedal 3.

In the following, the reason why the pedal 3 can only generate an unlocking action via the latch 4 will be described. The latch 4 and the pedal 3 are pressed respectively. For example, the latch 4 is pressed to output a second trigger signal. After the processor 6 receives the second trigger signal, the latch 4 is released. Then, after the first key 311 or the second key 321 of the pedal 3 is pressed, the pedal 3 outputs a first trigger signal. After the processor 6 receives the first trigger signal, since the processor 6 has received the first rigger signal and the second trigger signal respectively, the circuit board 2 is electrically connected to the pedal 3. Thus, pressing the first key 311 or the second key 321 outputs a driving signal for controlling the height and inclination angle of a sickbed or a clinic chair. The problem that the foot switch may be stepped on by mistake when the operator is busy or absentminded can be prevented. Therefore, the foot switch of the present invention has an improved safety in use.

Figure 9:
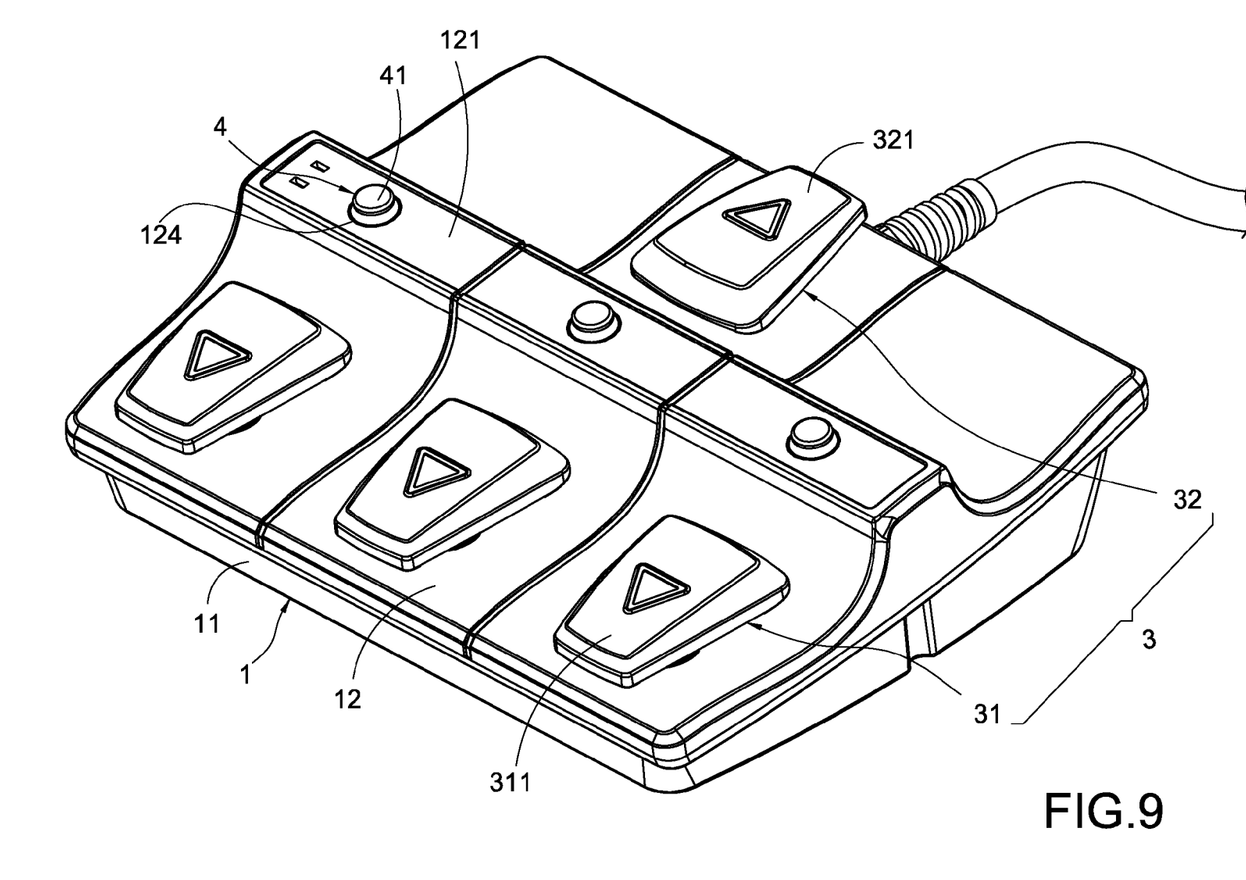
FIG. 9 is an assembled view showing the foot switch of a further embodiment of the present invention.
Figure 10:
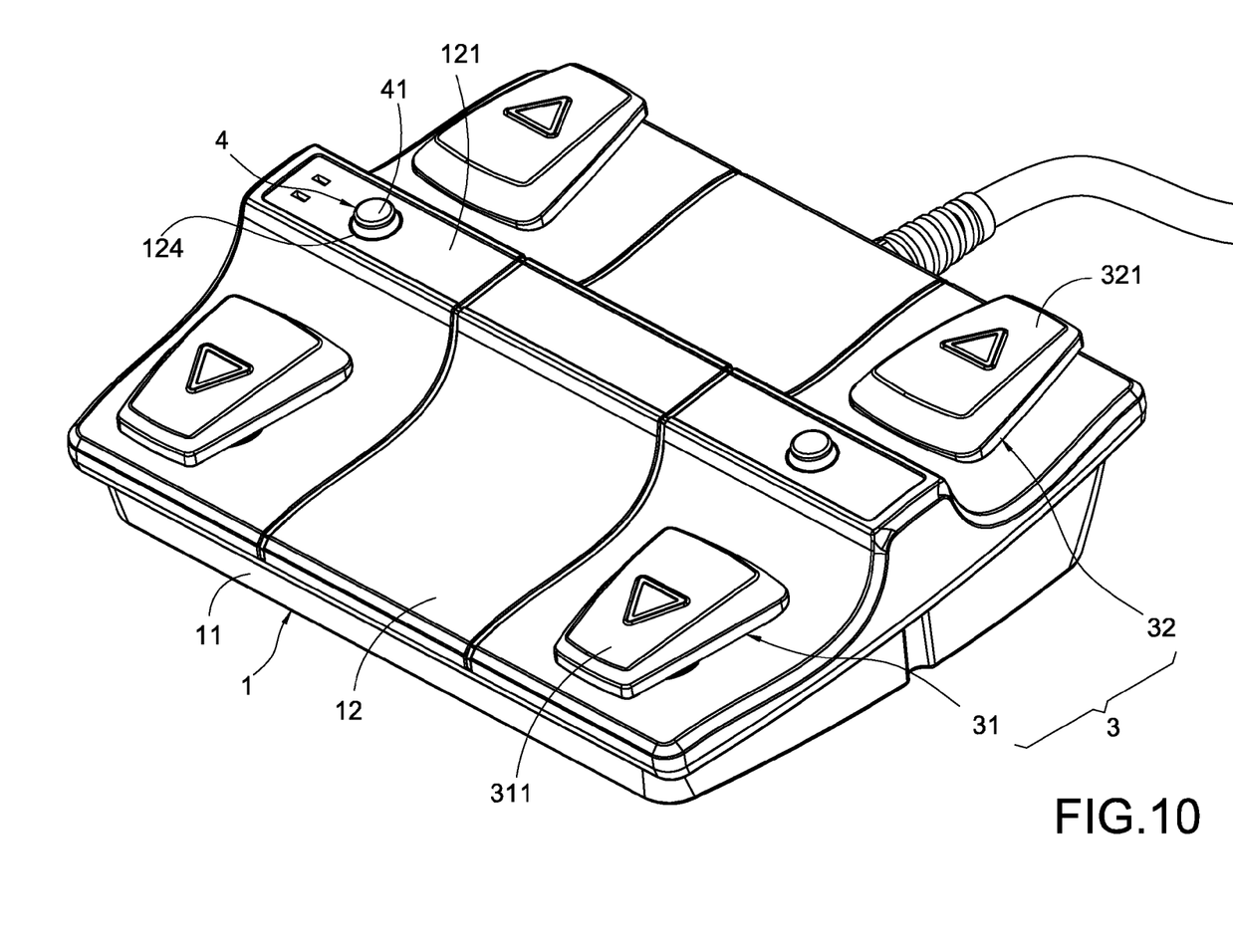
FIG. 10 is an assembled view showing the foot switch of still a further embodiment of the present invention.

Please refer to FIGS. 9 and 10, which show further embodiments of the present invention. The position and the number of the pedal 3 and the latch 4 in the main body 1 are not limited to those in the embodiments of FIGS. 1 to 6, and can be changed based on practical demands of the operator, the user or the manufacturer. As shown in FIG. 7 or 8, the position and the number of the pedal 3 and the latch 4 in the main body 1 is adjusted based on practical demands and are not limited to those shown in the figures.

Although the present invention has been described with reference to the foregoing preferred embodiments, it will be understood that the invention is not limited to the details thereof. Various equivalent variations and modifications can still occur to those skilled in this art in view of the teachings of the present invention. Thus, all such variations and equivalent modifications are also embraced within the scope of the invention as defined in the appended claims.

What is claimed is:

1. A foot switch having a security mechanism, including:
a main body having a cover, the cover having a top surface, and a protruding section protruding from the top surface;
a circuit board provided in the main body;
a pedal provided on the top surface of the main body; and
a latch provided on the protruding section and adjacent to the pedal, the latch being positioned at an elevated position with respect to the pedal, the pedal being electrically connected to the circuit board via the latch;
wherein the circuit board is electrically connected to the pedal when the latch and the pedal are pressed,
wherein the pedal comprises a first key and a second key, the first key and the second key are exposed to the main body, the latch is provided on the main body between the first key and the second key,
wherein the pedal comprises a first adjusting assembly and a second adjusting assembly, the first adjusting assembly comprises the first key and a first trigger switch connected to each other, the second adjusting assembly comprises the second key and a second trigger switch connected to each other,
wherein the main body comprises a base and the cover covering the base, the cover is provided with a through-hole, the first trigger switch is received in the base to be electrically connected to the circuit board, the first trigger switch has a first recovering portion, the first key passes through the through-hole and abuts against the first recovering portion, and
wherein the cover is provided with an annular block protruding from the periphery of the through-hole, the annular block is provided with an annular groove, the first key has a first supporting post and a first protruding block extending from the periphery of the first supporting post, the first protruding block is provided with a first trough, the first supporting post is disposed through the through-hole, the annular block and the first protruding block are engaged with the first trough via the annular groove.

2. The foot switch having a security mechanism according to claim 1, wherein the latch comprises a pressing button exposed to the protruding section, the first key and the second key are provided on two sides of the cover with the protruding section positioned therebetween.

3. The foot switch having a security mechanism according to claim 1, wherein the cover is provided with another through-hole, the second trigger switch is received in the base to be electrically connected to the circuit board, the second trigger switch has a second recovering portion, the second key passes through the another through-hole and abuts against the second recovering portion.

4. The foot switch having a security mechanism according to claim 3, wherein the cover is provided with another annular block protruding from the periphery of the another through-hole, the another annular block is provided with another annular groove, the second key has a second supporting post and a second protruding block extending from the periphery of the second supporting post, the second protruding block is provided with a second trough, the second supporting post is disposed through the another through-hole, the another annular block and the second protruding block are engaged with the second trough via the another annular groove.

5. The foot switch having a security mechanism according to claim 1, wherein the latch comprises the pressing button and a pressing switch connected to each other, and the latch is exposed to the main body.

6. The foot switch having a security mechanism according to claim 5, wherein the cover is provided with a penetration hole, the pressing switch is received in the base to be electrically connected to the circuit board, the pressing switch has a recovering portion, the pressing button abuts against the recovering portion via the penetration hole.

7. A foot switch having a security mechanism, including:
a main body having a cover, the cover having a top surface, and a protruding section protruding from the top surface;
a circuit board provided in the main body;
a pedal provided on the top surface of the main body;
a latch provided on the protruding section and adjacent to the pedal, the latch being positioned at an elevated position with respect to the pedal; and
a processor, the pedal and the latch being electrically connected to the circuit board via the processor;
wherein the pedal is pressed to output a first trigger signal, the latch is pressed to output a second trigger signal, the circuit board is electrically connected to the pedal when the processor receives the first trigger signal and the second trigger signal, wherein the pedal comprises a first key and a second key, the first key and the second key are exposed to the main body, the latch is provided on the main body between the first key and the second key, wherein the pedal comprises a first adjusting assembly and a second adjusting assembly, the first adjusting assembly comprises the first key and a first trigger switch connected to each other, the second adjusting assembly comprises the second key and a second trigger switch connected to each other, wherein the main body comprises a base and the cover covering the base, the cover is provided with a through-hole, the first trigger switch is received in the base to be electrically connected to the circuit board, the first trigger switch has a first recovering portion, the first key passes through the through-hole and abuts against the first recovering portion, and wherein the cover is provided with an annular block protruding from the periphery of the through-hole, the annular block is provided with an annular groove, the first key has a first supporting post and a first protruding block extending from the periphery of the first supporting post, the first protruding block is provided with a first trough, the first supporting post is disposed through the through-hole, the annular block and the first protruding block are engaged with the first trough via the annular groove.

8. The foot switch having a security mechanism according to claim 7, wherein the latch comprises a pressing button exposed to the protruding section, the first key and the second key are provided on two sides of the cover with the protruding section positioned therebetween.

9. The foot switch having a security mechanism according to claim 7, wherein the cover is provided with another through-hole, the second trigger switch is received in the base to be electrically connected to the circuit board, the second trigger switch has a second recovering portion, the second key passes through the another through-hole and abuts against the second recovering portion.

10. The foot switch having a security mechanism according to claim 9, wherein the cover is provided with another annular block protruding from the periphery of the another through-hole, the another annular block is provided with another annular groove, the second key has a second supporting post and a second protruding block extending from the periphery of the second supporting post, the second protruding block is provided with a second trough, the second supporting post is disposed through the another through-hole, the another annular block and the second protruding block are engaged with the second trough via the another annular groove.

11. The foot switch having a security mechanism according to claim 7, wherein the latch comprises the pressing button and a pressing switch connected to each other, and the latch is exposed to the main body.

12. The foot switch having a security mechanism according to claim 11, wherein the cover is provided with a penetration hole, the pressing switch is received in the base to be electrically connected to the circuit board, the pressing switch has a recovering portion, the pressing button abuts against the recovering portion via the through-hole.

* * * * *